United States Patent [19]

Ohno et al.

[11] Patent Number: 5,176,905
[45] Date of Patent: Jan. 5, 1993

[54] PHOTOCHROMIC FLESH-COLORED PIGMENT AND PROCESS FOR PRODUCING THE SAME

[75] Inventors: Kazuhisa Ohno, Oota; Shigenori Kumagai, Machida; Fukuji Suzuki, Atugi; Nobuhisa Tsujita, Machida, all of Japan

[73] Assignee: Shiseido Co., Ltd., Tokyo, Japan

[21] Appl. No.: 620,200

[22] Filed: Nov. 30, 1990

[30] Foreign Application Priority Data

Nov. 30, 1989 [JP] Japan .................. 1-312296

[51] Int. Cl.⁵ .................................. A61K 7/035
[52] U.S. Cl. .................................. 424/69; 424/63
[58] Field of Search ............ 424/69, 63; 106/418, 106/428, 430, 439

[56] References Cited

U.S. PATENT DOCUMENTS

| | | | |
|---|---|---|---|
| 3,869,298 | 3/1975 | Suzuki et al. | 106/418 |
| 3,926,659 | 12/1975 | Bernhard | 106/418 |
| 3,929,501 | 12/1975 | Dunn, Jr. | 106/439 |
| 4,084,984 | 4/1978 | Hund et al. | 106/286.3 |
| 4,804,532 | 2/1989 | Busch, Jr. | 424/69 |
| 4,919,726 | 4/1990 | Rademachers et al. | 106/428 |

FOREIGN PATENT DOCUMENTS 2313331  3/1973  Fed. Rep. of Germany ...... 106/418
5598261  7/1980  Japan .

Primary Examiner—Thurman K. Page
Assistant Examiner—David J. Colucci
Attorney, Agent, or Firm—Oliff & Berridge

[57] ABSTRACT

A photochromic flesh-colored pigment comprising not less than 90 wt % of anatase type titanium oxide having photochromism and a process for producing a photochromic flesh-colored pigment comprising the steps of adding iron hydroxide (FeOOH) to a composition containing untreated anatase type titanium oxide as the main ingredient, and calcining the mixture at 750° to 850° C. It is possible to exhibit a flesh color with a single color with a single pigment and it is also possible to change the color depending upon the intensity of light.

10 Claims, 1 Drawing Sheet

PHOTOCHROMIC FLESH-COLORED PIGMENT AND PROCESS FOR PRODUCING THE SAME

BACKGROUND OF THE INVENTION

1. Field of the Invention

The present invention relates to a photochromic flesh-colored pigment and a process for producing the same and, more particularly, to the improvement of a pigment using titanium oxide.

2. Description of the Prior Art

A flesh-colored pigment is essential as a cosmetic material, in particular, as a material of foundation. Since the flesh color is representative of a neutral tint tinged with warmth, a flesh-colored pigment is one of the pigments much in demand which is applied to various daily necessities.

It is hitherto difficult to produce a flesh-colored pigment from a single component, and general flesh-colored pigments are composed of an iron oxide pigment with an appropriate amount of red (red oxide $Fe_2O_3$), yellow (yellow oxide FeOOH) and black (black oxide $Fe_3O_4$) mixed therewith.

However, since the dispersibility is different depending upon the kind of iron oxide and, especially, red oxide and black oxide have poor dispersibilities, the pigment contains many grains. In addition, the pigment has a different color depending upon the mixing time. When the mixing time is long, a reddish color disadvantageously becomes vivid.

As a countermeasure, a skin cosmetic preparation bringing out a flesh color by a single pigment has been developed (see Japanese Patent Laid-Open No. 98009/1984). A flesh-colored pigment obtained by substantially uniformly coating the particle surfaces of titanium dioxide with at least one selected from the group consisting of hematite and amorphous hydrous iron oxide is provided.

Recently, a pigment is required to have various functions. For example, a pigment the tone of which varies with the optical conditions, in other words, a pigment provided with what is called photochromism (or phototropy) has attracted public attention.

As products to which such photochromism is applied, dimmer glass, color-variable make-up cosmetic preparation, etc. have conventionally been developed (see Japanese Patent Laid-Open No. 49312/1981 and 10079/1981), and application of photochromism to a wider field has been expected.

However, no flesh-colored pigment excellent in productivity and usability and provided with photochromism has yet been developed. In view of the wide application range of a flesh-colored pigment, the development of such a flesh-colored pigment has been strongly demanded.

SUMMARY OF THE INVENTION

Accordingly, it is an object of the present invention to eliminate the above-described problems in the prior art and to provide a flesh-colored pigment which is excellent in productivity and usability and which is provided with photochromism.

As a result of studies undertaken by the present inventors so as to achieve this aim, it has been found that a photochromic pigment containing anatase type titanium oxide as the main ingredient has a very good flesh color. The present invention has been achieved on the basis of this finding.

A photochromic flesh-colored pigment according to the present invention comprises not less than 90 wt % of anatase type titanium oxide having photochromism.

A process for producing a photochromic flesh-colored pigment according to the present invention comprises the steps of adding iron hydroxide (FeOOH) to a composition which contains untreated anatase type titanium oxide as the main ingredient and calcining the mixture at a temperature of 750° to 850° C.

The titanium oxide is preferably anatase type titanium oxide having an average particle diameter of about 0.3 μm and not subjected to a surface treatment.

The iron hydroxide is preferably acicular or rod-like iron hydroxide having a particle diameter of 0.075 to 0.6 μm.

The mixing ratio of iron hydroxide to the untreated anatase type titanium oxide is preferably about 1 part to 99 parts.

The structure of the present invention will be explained in more detail.

Titanium oxide in the present invention is mainly composed of anatase type titanium oxide. If not less than 10 wt % of rutile or amorphous titanium oxide is contained, the tone changes from a flesh color to yellowish brown, and the pigment produced cannot be said to be a flesh-colored pigment. This is because the increase of rutile titanium oxide and the like enhances the brightness of the flesh color and tinges it with yellow.

In order to impart photochromism to anatase type titanium oxide, it is preferable to add iron hydroxide (FeOOH) to a composition which contains untreated anatase type titanium oxide as the main ingredient and calcine the mixture at a temperature of 750° to 850° C.

If the temperature is lower than 750° C., photochromism is not exhibited. On the other hand, if the temperature is higher than 850° C., anatase type titanium oxide changes into rutile titanium oxide and the pigment produced takes on a yellowish brown color.

Use of a photochromism activating agent other than iron hydroxide (FeOOH) cannot produce a good flesh-colored pigment.

In the present invention, it is possible to use a flesh-colored pigment in the form of a composite with another inorganic or organic compound. For example, it is possible to make a composite by mixing, coating or sintering at least one selected from the group consisting of: an inorganic compound such as mica, sericite, talc, kaolin, silica, barium sulfate, iron oxide, chromium oxide, copper oxide, nickel oxide, vanadium oxide, manganese oxide, cobalt oxide, calcium oxide, magnesium oxide, molybdenum oxide, zinc oxide, iron, chromium, copper, nickel, vanadium and manganese; and an organic compound such as nylon, polymethyl methacrylate, polystyrene, epoxy resin and polyethylene; with a photochromic flesh-colored pigment.

It is also preferable to impart photochromism to anatase type titanium oxide after it is made a composite with another inorganic or organic compound.

A composite containing a photochromic flesh-colored pigment is produced, for example, by the following methods. In the case of a titanium dioxide-coated composite such as titanium-mica and titanium-talc, 0.05 to 5.0 wt % of iron hydroxide based on the amount of titanium dioxide is added to the titanium dioxide-coated composite by using a ball mill and a Henschel mixer in a dry process or in the form of an aqueous solution by a wet process, and the composite is thereafter calcined at 750° to 850° C. Alternatively, a titanium dioxide composite is obtained by the hydrolysis of titanyl sulfate in the presence of iron oxide, and the composite is thereafter calcined at 750° to 850° C.

A photochromic flesh-colored pigment or a composite containing a photochromic flesh-colored pigment of the present invention may be further subjected to a surface treatment with silicon, surfactant, metallic soap, fatty acid, fluoroplastic, wax or the like, or the surface thereof may be alkoxilated. A combination of these surface treatments may be adopted. If the dispersibility of the pigment is enhanced by the surface treatment, it is possible to further enhance the photochromism.

In the case of applying a photochromic flesh-colored pigment of the present invention to a cosmetic preparation, it is possible to blend other components which are generally used in the composition of a cosmetic preparation, as occasion demands. For example, it is possible to blend an inorganic powder such talc, kaolin, sericite, muscovite, phlogopite, synthetic mica, lepidolite, biotite, lithia mica, vermiculite, magnesium carbonate, calcium carbonate, diatomaceous earth, magnesium silicate, calcium silicate, aluminum silicate, barium silicate, barium sulfate, strontium silicate, metal salt of tungstic acid, silica, magnesium oxide, calcium oxide, zeolite, boron nitride and ceramic powder; an organic powder such as nylon powder, polyethylene powder benzoguanamine powder, ethylene tetrafluoride powder and microcrystalline cellulose; a hydrocarbon such as squalane, liquid paraffin, vaseline, microcrystalline wax, ozocerite, ceresine, cetyl alcohol, haxadecyl alcohol, oleyl alcohol, cetyl-2-ethyl hexanoate, 2-ethylhexyl palmitate, 2-octyldodecyl myristate, 2-octyldodecyl gum ester, neopentyl glycol-2-ethyl hexanoate, isooctylic acid triglyceride, 2-octyldodecyl oleate, isopropyl myristate, isostearic acid triglyceride, coconut fatty acid triglyceride, olive oil, avocado oil, beeswax, myristyl myristate, zinc oxide, lanolin and dimethyl polysiloxane; an oil content such as oil, fat, ester, higher alcohol, wax, silicone oil and silicone resin; an ultraviolet light absorbent; antioxidant; antiseptic agent; surfactant; humectant; perfume; water; alcohol; and thickening agent.

In the case of applying a photochromic flesh-colored pigment of the present invention to a cosmetic preparation, a cosmetic preparation can take the form of a powder, cake, pencil, stick, ointment, liquid, milky lotion, cream or the like.

The above and other objects, features and advantages of the present invention will become clear from the following description of the preferred embodiments thereof, taken in conjunction with the accompanying drawings.

DESCRIPTION OF THE PREFERRED EMBODIMENTS

Figure 1:
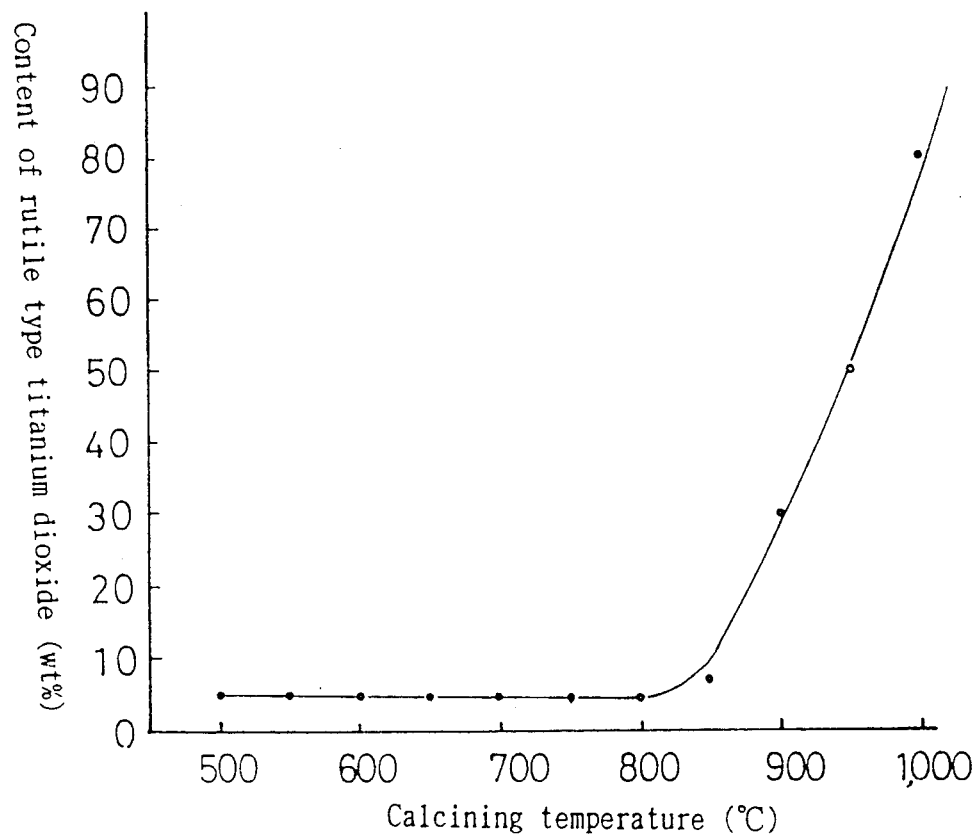
FIG. 1 explains the relationship between the calcining temperature and the increase in the content of rutile titanium oxide due to rearrangement.

The present invention will be explained in more detail hereinunder with reference to embodiments.

Definition of Flesh Color

The flesh color in the present invention refers to the color satisfying the following relationships when a sample obtained by forming coating film on paper using 76 μm applicator, and the coating is made of 4 g of a powder dispersed in 16 g of nitrocellulose, and tested by a calorimeter (Minolta CR-200):

$82.5 \leq L \leq 84.5$ $11.5 \leq a \leq 14.0$ $11.5 \leq b \leq 13.5$

The flesh color in the present invention refers to the color satisfying the following relationships when a sample obtained by forming 5 g of a powder in a medium-size square plate of 2.8×4.5 cm under a pressure of 30 Kg/cm$^2$ and tested by a calorimeter (Minolta CR-200):

Accordingly, in the case of such powder forming, the following relationships are preferably satisfied:
 H = 8 R to 4 YR
 V = 8.0 to 9.0
 C = 1.8 to 2.5
More preferably
 H = 9 R to 3 YR
 V = 8.5 to 8.9
 C = 1.9 to 2.0

Definition of Photochromism

The photochromism was tested in the following manner in the present invention.

The photochromism was in the following manner in the present invention.

A sample was produced by forming 5 g of a powder in a medium-size square plate of 2.8×4.5 cm under a pressure of 30 Kg/cm$^2$.

As to the optical conditions, one UV-A fluorescent lamp (FL20SBLB, produced by Toshiba Co., Ltd.) and one UV-B fluorescent lamp (FL20S.E, produced by Toshiba Co., Ltd.) were fixed at an interval of 15 cm, and using an ultraviolet light intensity measuring machine (SUV-T, produced by Toray Co., Ltd.), the height was adjusted so that the intensity of ultraviolet light was 2 mW/cm$^2$.

The actual measurement was carried out in the following manner.

(1) The sample which had been allowed to stand in a darkroom at room temperature for about 10 hours was measured by a calorimeter (Minolta CR-200).
(2) The sample was placed at the height and irradiated with ultraviolet light by the above-described ultraviolet light intensity for 30 minutes, and the darkened color was measured in the same way as described in (1).
(3) After the darkened sample was allowed to stand in the dark room for 3 hours, it was measured in the same way as described in (1).

The photochromism is defined by $3 \leq A \leq 12$ $B \leq 2$ wherein A represents the color difference ΔE between (1) and (2), and B represents the color difference ΔE between (1) and (3).

Anatase Type Titanium Oxide

It is essential in the present invention that the content of anatase type titanium oxide is not less than 90 wt % when photochromism is imparted to titanium oxide.

Since anatase type titanium oxide is converted into rutile titanium oxide by rearrangement when anatase type titanium oxide is calcined so as to impart photochromism thereto, the control of the calcining temperature is very important.

If the calcining temperature is high, the content of rutile titanium oxide increases, which inconveniently change the color of the pigment from a flesh color to yellowish brown (the brightness is enhanced and a yellow color become vivid). If the yellow color becomes more vivid than a flesh color, the pigment cannot be said to be a flesh-colored pigment any longer.

This state is shown in FIG. 1. A material titanium oxide containing not less than 95% of anatase type titanium oxide (not more than 5% of rutile titanium oxide) was calcined for 6 hours. It is observed from FIG. 1 that although almost no change is caused in the content of rutile titanium oxide up to 850° C., rearrangement rapidly progresses in the vicinity of the point immediately above 850° C., the content of rutile titanium oxide exceeds 40 wt % at 900° C., and when the temperature reaches 1,000° C., the anatase type titanium oxide is converted into approximately 100% rutile titanium oxide by rearrangement.

Figure 2:
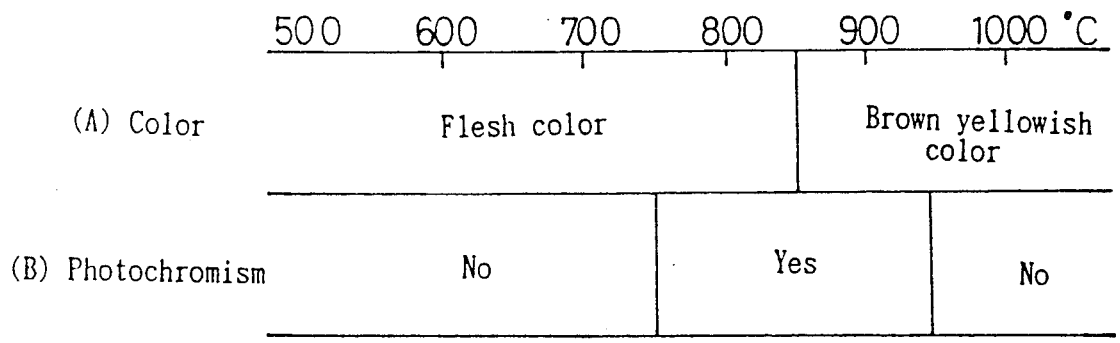
FIG. 2 explains the relationship between the calcining temperature and the tone and the photochromism of the pigment.

With this phenomenon, the tone begins to rapidly change from a flesh color to a brown yellowish color at 850° C., as shown in FIG. 2(A). Such a brown yellowish pigment cannot be said to be a flesh-colored pigment.

The content of rutile titanium oxide here is significant for imparting photochromism and does not except, for example, the case of adding rutile titanium oxide after photochromism is imparted.

When a flesh-colored pigment was produced from anatase type titanium oxide having an average particle diameter of 0.1 to 0.5 μm and more preferably about 0.3 μm, and subjected to no surface treatment, a flesh-colored pigment having a good photochromism was obtained.

In contrast, when the surface of anatase type titanium oxide was treated with silica alumina or the like, $\Delta E$ was apparently reduced.

When rutile titanium oxide subjected to a surface treatment was used as a raw material and calcined, $\Delta E$ was approximately zero. In the case of using untreated rutile titanium oxide, a color change due to ultraviolet was very small, and $\Delta E$ was about 1 to 2.

The reason why the average particle diameter of anatase type titanium oxide was set at 0.3 μm, the coloring power was maximal in the vicinity thereof. When anatase type titanium oxide and rutile titanium oxide having an average particle diameter of 0.03 μm were used in the weight ratio of 7:3, the pigment produced was unfavorably rough and the opacyfying power was low probably because the particles sintered between each other.

Photochromism

The photochromism also has a close relation to the calcining temperature. As shown in FIG. 2(B), anatase titanium oxide cannot be invested with photochromism unless it is calcined at a temperature of not lower than 750° C.

On the other hand, if anatase titanium oxide is calcined at a temperature of not lower than 950° C., the photochromism is reduced. It is observed from FIG. 2(B) that the calcining temperature suitable for imparting photochromism is in the range of 750° to 950° C.

It is therefore necessary to calcine anatase titanium oxide at 750° to 850° C. in order to obtain a photochromic flesh-colored pigment.

Photochromism Activating Agent

In order to impart photochromism to a titanium oxide, a metal such as iron, chromium, copper, nickel, manganese, cobalt and molybdenum is generally used. These metals are used in the form of metal powders itself, salts such as sulfates, chlorides, nitrates and acetates, oxides or hydrate.

In the present invention, however, these metals cannot be used and it is necessary to use iron hydroxide (FeOOH) as a photochromism activating agent.

Use of other iron compounds such as iron sulfate ($FeSO_4 \cdot 7H_2O$) produces a white or yellowish brown pigment, and cannot produce a flesh-colored pigment in accordance with the present invention.

When acicular iron hydroxide of a commercial grade (particle diameter of FeOOH: 0.075 to 0.6 μm) was used, a good photochromic flesh-colored pigment was obtained. If the particle diameter was approximately the same, rod-like iron hydroxide produced a similar effect.

When fine iron hydroxide (diameters: 0.02 to 0.04 μm) was used, the pigment took on a yellowish brown color at the time of calcination, and a flesh-colored pigment was not obtained.

The preferable mixing ratio is about 1 part by weight of acicular FeOOH to 99 parts by weight of untreated anatase titanium oxide.

With the increase in the amount of iron hydroxide added, $\Delta E$ tends to be reduced. When 5 wt % of iron hydroxide is added, almost no color change ($\Delta E$ is not more than 1.5) is caused due to light radiation.

The content of iron hydroxide here is significant for imparting photochromism and does not except, for example, the case of adding iron hydroxide after photochromism is imparted.

The structure of the present invention will be explained in more detail in the following with respect to the following examples.

In the following examples, a photochromic flesh-colored pigment was used which was obtained by adding 1.1 parts by weight of acicular iron hydroxide to 99 parts by weight of untreated anatase titanium oxide and calcining the mixture at about 800° C. for 4 hours.

EXAMPLE 1

Powder Foundation

|   |   | wt % |
|---|---|---|
| (1) | Photochromic flesh-colored pigment | 20.0 |
| (2) | Talc | 10.0 |
| (3) | Sericite | 49.5 |
| (4) | Spherical nylon powder | 8.0 |
| (5) | Polydimethyl siloxane | 5.0 |
| (6) | 2-ethylhexyl palmitate | 5.0 |
| (7) | Solbitan sesquioleate | 1.0 |
| (8) | Antiseptic agent | 0.9 |
| (9) | Perfume | 0.1 |

The ingredients (1) to (6) were mixed by a Henschel mixer and to the mixture the ingredients (7) to (9) which had been melted and mixed under heating were added. The resultant mixture was pulverized by a pulverizer (Hosokawa Micron). The pulverized mixture was formed in a medium-size plate so as to obtain a powder foundation.

The thus-obtained powder foundation containing a photochromic flesh-colored pigment can exhibit a flesh color without adding another pigment. In addition, since the color changes depending upon the intensity of light, the pigment can exhibit a corn color suggestive of a beautifully-tanned skin under the sunlight, while it exhibits a slightly light flesh color, which is elegant, in a room.

EXAMPLE 2

Water-Soluble Powder Foundation

| | | wt % |
|---|---|---|
| (1) | Photochromic flesh-colored pigment | 31.0 |
| (2) | Silicone-Treated mica | 36.0 |
| (3) | Silicone-treated talc | 20.0 |
| (4) | Trimethylol propane triisostearate | 5.0 |
| (5) | Squalane | 3.0 |
| (6) | Beeswax | 2.0 |
| (7) | Solbitan trioleate | 1.0 |
| (8) | Antiseptic agent | 0.5 |
| (9) | Vitamin E | 0.05 |
| (10) | Butylmethoxy benzoylmethane | 1.0 |
| (11) | Perfume | 0.2 |

The ingredients (1) to (3) were mixed, and to the mixture the ingredients (4) to (11) which had been melted and mixed under heating were added. The resultant mixture was pulverized and formed in a medium-size plate so as to obtain a water-soluble foundation.

EXAMPLE 3

Suntan oil

| | | wt % |
|---|---|---|
| (1) | Liquid paraffin | 69.75 |
| (2) | Silicone oil | 20.0 |
| (3) | Vitamin E | 0.05 |
| (4) | Perfume | 0.2 |
| (5) | Photochromic flesh-colored pigment | 10.0 |

The ingredients (1) to (4) were mixed, and after the ingredient (5) was added to and dispersed in the mixture, the resultant mixture was deaerated to obtain suntan oil. This suntan oil exhibited a corn color suggestive of a beautifully-tanned skin under the sunlight and was also excellent in the ultraviolet light preventive effect.

EXAMPLE 4

Coating

| | | wt % |
|---|---|---|
| (1) | Photochromic flesh-colored pigment | 10.0 |
| (2) | Acryloid B-66 | 22.0 |
| (3) | Xylene | 48.0 |
| (4) | Mineral spirit | 20.0 |

The ingredients (1) to (3) were kneaded by a roll mill to obtain an acrylic coating.

The thus-obtained photochromic coating was applied to a wall and the brightness of the room was varied. The wall exhibited a whitish flesh color under dark light, while it exhibited a slightly dark subdued flesh color under bright light.

EXAMPLE 5

Emulsified Foundation

| | | wt % |
|---|---|---|
| (1) | Photochromic flesh-colored pigment | 1.5 |
| (2) | Stearic acid | 1.5 |
| (3) | Isostearic acid | 0.3 |
| (4) | Isopropyl myristate | 4.0 |
| (5) | Squalane | 12.0 |
| (6) | POE stearyl ether | 1.5 |
| (7) | Glyceryl monooleate | 0.5 |
| (8) | Cetyl alcohol | 0.5 |
| (9) | Talc | 10.0 |
| (10) | Antiseptic agent | 0.15 |
| (11) | Triethanol amine | 0.8 |
| (12) | Propylene glycol | 6.0 |
| (13) | Montmorilonite | 0.5 |
| (14) | Purified water | 60.55 |
| (15) | Perfume | 0.2 |

The ingredients (11) to (14) were mixed and heated to 70° C. To the mixture, the ingredients (2) to (8), (10) and (15) which had been melted and mixed under heating were slowly added, emulsified and dispersed. The resultant mixture was cooled to room temperature to obtain emulsified foundation.

This emulsified foundation was applied to the face. Under the sunlight, the brightness of the color of the skin was lowered. Thus, the made-up skin gave the feeling of naturalness and beauty both in the room and outdoors.

EXAMPLE 6

Nail Enamel

| | | wt % |
|---|---|---|
| (1) | Alkyd resin | 10.0 |
| (2) | Proxyline | 13.0 |
| (3) | Acetyltributyl citrate | 5.0 |
| (4) | Organic modified montmorilonite | 1.0 |
| (5) | Toluene | 21.0 |
| (6) | Butyl acetate | 37.7 |
| (7) | Ethyl acetate | 5.3 |
| (8) | n-butanol | 2.0 |
| (9) | Lithol Rubine BCA | 0.3 |
| (10) | Photochromic flesh-colored pigment | 4.7 |

The ingredients (5) to (8) were mixed, and the ingredients (1) to (3) were added to the mixture. Thereafter, the ingredients (4), and (9) to (10) were added to and dispersed in the resultant mixture.

The color of the nail enamel changed under the sunlight. Thus, a relishable nail enamel was obtained.

EXAMPLE 7

Emulsified Foundation in Compact

| | | wt % |
|---|---|---|
| (1) | Decamethylcyclopentasiloxane | 20.0 |
| (2) | Dimethylpolysiloxane (6 cs) | 5.0 |
| (3) | Jojoba oil | 1.0 |
| (4) | Paraffin wax | 6.0 |
| (5) | Microcrystalline wax | 4.0 |
| (6) | Polyoxyalkylene-modified organopolysiloxane | 3.0 |
| (7) | Hydrophobic photochromic flesh-colored pigment | 26.0 |
| (8) | Hydrophobic iron oxide pigment | 4.0 |
| (9) | Ion-exchanged water | 10.0 |

-continued

|      |                  | wt %            |
|------|------------------|-----------------|
| (10) | Glycerin         | 8.0             |
| (11) | 1,3 butylene glycol | 2.0          |
| (12) | Antiseptic agent | proper quantity |
| (13) | Perfume          | proper quantity |

The ingredients (1) to (6), and (13) were heated to 80° C., and the ingredients (7) and (8) were added to and dispersed in the mixture. The mixture of ingredients (9) to (12) which had been heated to 80° C. were added and the resultant mixture was emulsified and dispersed. The emulsion in a liquid state was charged into a medium-size plate and cooled to room temperature. The product was then charged in a compact to obtain the target emulsified foundation in a compact.

In this example, since the photochromic flesh-colored pigment which had been treated so as to be hydrophobic was used, the dispersibility was good and photochromism was sufficient.

Other Uses

A photochromic flesh-colored pigment according to the present invention is applicable to the following uses in addition to the above-described preparations and coating.

- Gatepost: The gatepost to which the photochromic flesh-skin pigment is applied exhibits a slightly dark subdued flesh color in the daytime, while in the nighttime, the whitish color becomes vivid, thereby making itself conspicuous.
- Coating or fibers for military camouflage (chameleon fibers)
- Wears the colors of which change into bright colors under the bright sunlight
- Wig, lipstick, rouge, mascara (dramatic change)
- Doll the skin color of which changed under the sunlight
- Coating for architecture or automobile
- Simple actinometer
- Hologram (reversible optical memory material)
- Photograph dispensed with the need for development
- Hard copy for a newspaper transmitted by radio
- Monitor for frozen food (a pigment with the color changed by ultraviolet light is pasted to frozen food so as to monitor it and judge the frozen state on the basis of fading)
- Glaze for pottery
- Information display screen
- Photochromic frame of glasses
- Reversible photochromic thread
- Cover mark
- Reversible photochromic cloth
- Helmet, sun visor
- Decorative laminate
- Photochromic screen
- Ink
- Microcapsuled articles
- Printing on containers of cosmetics
- Marking pen and ball-point pen
- Printed letters and patterns which are developed by light
- Answers to questions in a study book or quizzes
- Magazine, leaflets, newspapers, papers.

As described above, according to a photochromic flesh-colored pigment of the present invention, it is possible to exhibit a flesh color with a single pigment and it is also possible to change the color depending upon the intensity of light.

According to a process for producing a photochromic of the present invention, it is possible to easily provide a homogeneous flesh-colored pigment.

What is claimed is:

1. A photochromic flesh-colored pigment comprising not less than 90 wt % of anatase titanium oxide having photochromism.

2. A photochromic flesh-colored pigment according to claim 1, wherein said titanium oxide is anatase titanium oxide having an average particle diameter of 0.1 to 0.5 μm and not subjected to any surface treatment.

3. A process for producing a photochromic flesh-colored pigment comprising the steps of adding iron hydroxide (FeOOH) to a composition containing not less than 90% by weight of untreated anatase titanium oxide as the main ingredient and calcining the mixture at 750° C. to 850° C.

4. A process for producing a photochromic flesh-colored pigment according to claim 3, wherein said iron hydroxide is acicular or rod-like iron hydroxide having a particle diameter 0.075 to 0.6 μm.

5. A process for producing a photochromic flesh-colored pigment according to either of claims 3 and 4, wherein the mixing ratio of said iron hydroxide to said untreated anatase titanium oxide is about 1 to 99 by part by weight.

6. A process for producing a photochromic flesh-colored pigment comprising the steps of adding in a dry or wet process 0.05–5.0 wt % of iron hydroxide based on an amount of titanium oxide in a titanium dioxide-coated composite to said titanium dioxide-coated composite which contains not less than 90% by weight of untreated anatase titanium oxide as the main ingredient; and calcining the mixture at 750°–850° C.

7. A process for producing a photochromic flesh-colored pigment comprising the steps of: producing untreated anatase titanium dioxide-coated composite by the hydrolysis of titanyl sulfate in the presence of 0.05 to 5.0 wt % of iron oxide, and calcining said composite at 750° to 850° C.

8. A process for producing a photochromic flesh-colored pigment comprising the steps of:
adding in a dry or wet process 0.05 to 5.0 wt % of iron hydroxide based on the amount of titanium dioxide in a titanium dioxide-coated composite comprising titanium-mica and titanium-talc to said titanium dioxide-coated composite containing not less than 90% untreated anatase titanium oxide as the main ingredient; and calcining the mixture at 750 to 850 C.

9. A process according to claim 6, wherein said titanium dioxide-coated composite comprises titanium oxide and at least one member selected from the group consisting of mica, sericite, talc, kaolin, silica, barium sulfate, iron oxide, chromium oxide, copper oxide, nickel oxide, vanadium oxide, manganese oxide, cobalt oxide, calcium oxide, magnesium oxide, molybdenum oxide, zinc oxide, iron, chromium, copper, nickel, vanadium, manganese, nylon, polymethyl methacrylate, polystyrene, epoxy resin and polyethylene.

10. A process according to claim 6, wherein said titanium dioxide-coated composite comprises titanium oxide and sericite.

* * * * *